United States Patent [19]

Horikawa

[11] Patent Number: 4,885,467
[45] Date of Patent: Dec. 5, 1989

[54] SHADING ELIMINATION METHOD

[75] Inventor: Kazuo Horikawa, Kanagawa, Japan

[73] Assignee: Fuji Photo Film Co., Ltd., Kanagawa, Japan

[21] Appl. No.: 205,243

[22] Filed: Jun. 10, 1988

[30] Foreign Application Priority Data

Jun. 10, 1987 [JP] Japan ................................ 62-144980

[51] Int. Cl.⁴ ...................... G01N 23/04; H04M 1/40
[52] U.S. Cl. .................................. 250/327.2; 358/163
[58] Field of Search .................. 250/484.1 B, 327.2 R, 250/327.2 A, 327.2 D, 327.2 E, 327.2 F, 327.2 G; 358/163, 280, 283

[56] References Cited

U.S. PATENT DOCUMENTS

| | | | |
|---|---|---|---|
| 4,258,264 | 3/1981 | Kotera et al. | 250/459.1 |
| 4,346,295 | 8/1982 | Tanaka et al. | 250/337 |
| 4,520,395 | 5/1985 | Abe | 358/163 |
| 4,523,229 | 6/1985 | Kanmoto | 358/163 |
| 4,524,388 | 6/1985 | Abe et al. | 358/163 |
| 4,633,314 | 12/1986 | Kurata et al. | 358/163 |
| 4,734,783 | 3/1988 | Horikawa | 358/280 |
| 4,818,876 | 4/1989 | Agano et al. | 250/484.1 B |

FOREIGN PATENT DOCUMENTS 56-11395  2/1981  Japan ................................ 250/327.2
0209430  9/1986  Japan ................................ 250/327.2 G Primary Examiner—Janice A. Howell
Assistant Examiner—William F. Rauchholz
Attorney, Agent, or Firm—Sughrue, Mion, Zinn, Macpeak & Seas

[57] ABSTRACT

Shading is eliminated in an image read-out apparatus for scanning a light beam on a recording medium carrying an image recorded thereon, obtaining light which carries the image by the scanning, and detecting the light by use of a photomultiplier to obtain read-out signals carrying the image. A shading elimination method comprises the steps of detecting the shading characteristics in the direction of main scanning of the light beam by changing the level of high voltage applied to the photomultiplier to a plurality of levels prior to the detection of the light, and storing the shading characteristics to correspond to the levels of the high voltage in a memory. The level of the high voltage is detected at the time of the detection of the light, and the shading characteristics that correspond to the detected level of the high voltage are read from the memory. The read-out signals are corrected in accordance with the shading characteristics read from the memory so that changes in the output of the photomultiplier caused by the shading are eliminated.

4 Claims, 4 Drawing Sheets

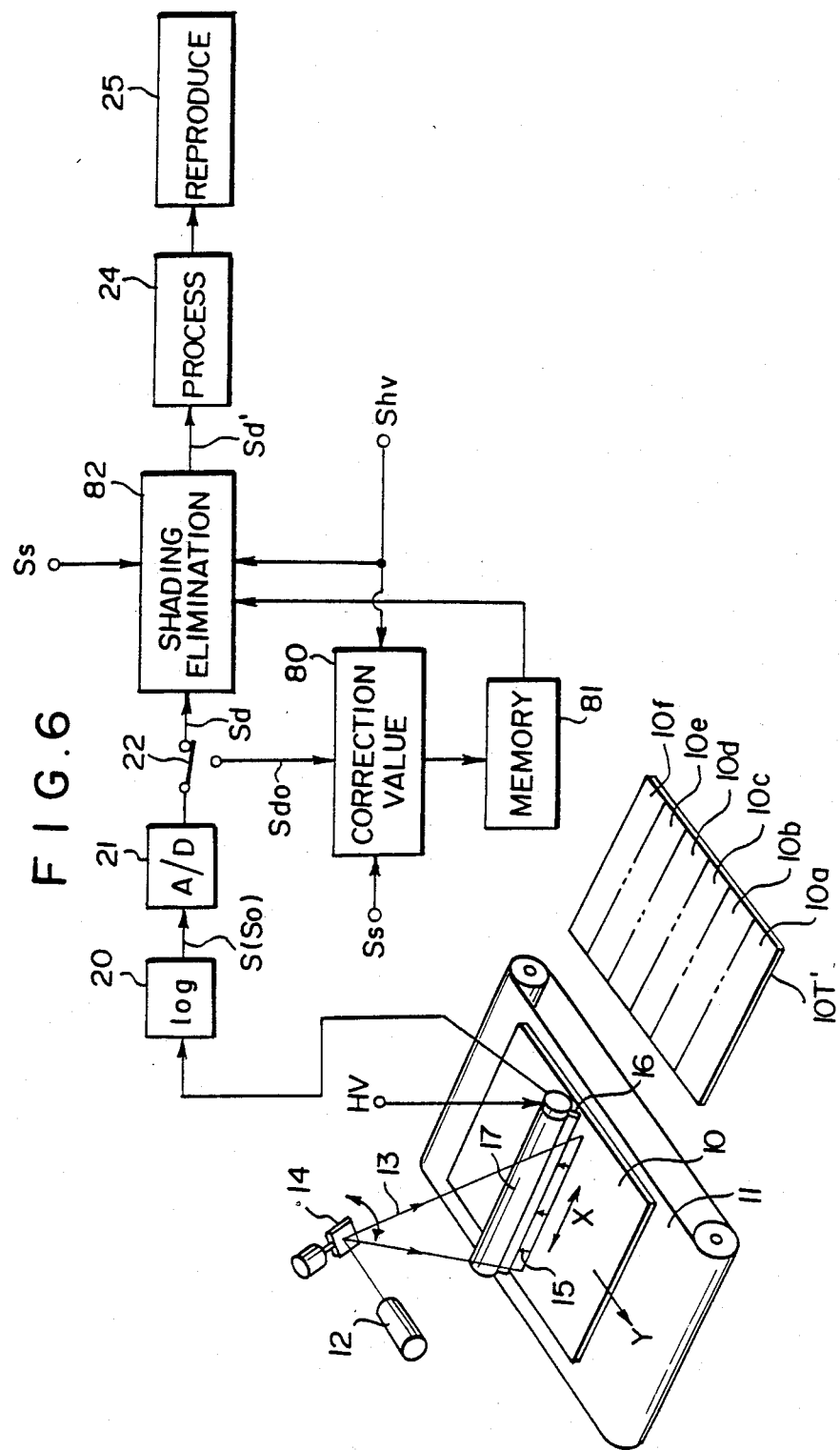

SHADING ELIMINATION METHOD

BACKGROUND OF THE INVENTION

1. Field of the Invention

This invention relates to a method of compensation for changes in the output of read-out signals caused by shading in an apparatus for reading out an image by scanning a light beam on a recording medium carrying the image recorded thereon, obtaining light which carries the image by the scanning, and detecting the light by a photomultiplier.

2. Description of the Prior Art

Image read-out apparatuses for reading out an image by scanning a light beam on a recording medium carrying the image recorded thereon and detecting light reflected by the recording medium, light passing through the recording medium, or light emitted by the recording medium 15 have heretofore been used as, for example, image input means for computers and image read-out means of facsimiles. Also, as one of the image read-out apparatuses of this type, there has heretofore been known a radiation image read-out apparatus as disclosed in, for example, U.S. Pat. No. 4,346,295 wherein a stimulable phosphor sheet carrying a radiation image of an object such as the human body stored thereon is scanned by stimulating rays which cause the stimulable phosphor sheet to emit light in proportion to the stored radiation energy, and the light emitted by the sheet portion exposed to stimulating rays is detected to obtain image signals representing the radiation image.

As one of photodetectors used in the aforesaid image read-out apparatus, there has heretofore been known a long photomultiplier as disclosed in, for example, Japanese Unexamined Patent Publication No. 62(1987)-16666. The long photomultiplier has a substantially long light receiving face which extends along a main scanning line on a recording medium. With the long photomultiplier, nonuniformity of the light receiving sensitivity arises in the longitudinal direction of the photomultiplier.

Also, the output of the photodetector may change due to nonuniformity of the intensity of the scanning light beam caused by nonuniformity of the reflectivity of a reflecting surface of a light deflector for deflecting the light beam in the main scanning direction, nonuniformity of the scanning speed of the light beam caused by fluctuations in the deflection speed of the light deflector, or light guiding nonuniformity of a light guide member provided for efficiently guiding the light obtained by the recording medium to the light receiving face of the photomultiplier, i.e. nonuniformity of the light guiding efficiency at, for example, an end portion of the photodetector. In the case where partial deterioration of the light detecting efficiency (i.e. shading) is caused by the aforesaid nonuniformities, it becomes impossible to accurately detect the light obtained by the recording medium.

In order to eliminate the aforesaid problems, there has been proposed a shading elimination method wherein shading characteristics in the direction of main scanning of a light beam are detected and stored prior to detection of light obtained by a recording medium, and read-out signals obtained by a photomultiplier are corrected in accordance with the shading characteristics at the time of the detection of the light so that output fluctuations caused by the shading are eliminated.

Basically, the proposed shading elimination method provides good results. However, the inventors found that nonuniformity characteristics of the light receiving sensitivity of the photomultiplier changes slightly when the high voltage applied to the photomultiplier is changed. In the case where nonuniformity characteristics of the light receiving sensitivity of the photomultiplier changes in this manner, it may occur that the shading characteristics detected in advance and the actual shading characteristics at the time image read-out processing is being carried out do not coincide with each other. As a result, shading elimination cannot be carried out accurately with respect to the actual shading characteristics.

SUMMARY OF THE INVENTION

The primary object of the present invention is to provide a method of eliminating the shading in an image read-out apparatus very accurately.

Another object of the present invention is to provide a shading elimination method in an image read-out apparatus which enables accurate detection of light carrying an image, and accurate reproduction of the image recorded on a recording medium.

The present invention was made based on the findings that fluctuations of nonuniformity characteristics of the light receiving sensitivity of a photomultiplier are caused by changes in the level of high voltage applied to the photomultiplier.

Specifically, the present invention provides a shading elimination method in an image read-out apparatus for scanning a light beam on a recording medium carrying an image recorded thereon, obtaining light which carries the image by the scanning, and detecting the light by use of a photomultiplier to obtain read-out signals carrying the image, the shading elimination method in an image readout apparatus which comprises the steps of:

(i) detecting the shading characteristics in the direction of main scanning of said light beam by changing the level of high voltage applied to said photomultiplier to a plurality of levels prior to said detection of said light, (ii) storing said shading characteristics to correspond to said levels of said high voltage in a storage means, (iii) detecting the level of said high voltage at the time of said detection of said light, and reading said shading characteristics that correspond to the detected level of said high voltage from said storage means, and (iv) correcting said read-out signals in accordance with said shading characteristics read from said storage means so that changes in the output of said photomultiplier caused by the shading are eliminated.

With the shading elimination method in accordance with the present invention, shading can be eliminated accurately, the light carrying the image can be detected accurately, and the image that was recorded on the recording medium can be reproduced accurately.

Also, with the shading elimination method in accordance with the present invention wherein the elimination of shading is carried out by considering fluctuations in the characteristics of shading caused by differences in the high voltage applied to the photomultiplier, shading can be eliminated very accurately.

BRIEF DESCRIPTION OF THE DRAWINGS

FIG. 6 is a schematic view showing a further example of the radiation image read-out apparatus wherein a further embodiment of the shading elimination method in accordance with the present invention is employed.

DESCRIPTION OF THE PREFERRED EMBODIMENTS

The present invention will hereinbelow be described in further detail with reference to the accompanying drawings.

Figure 1:
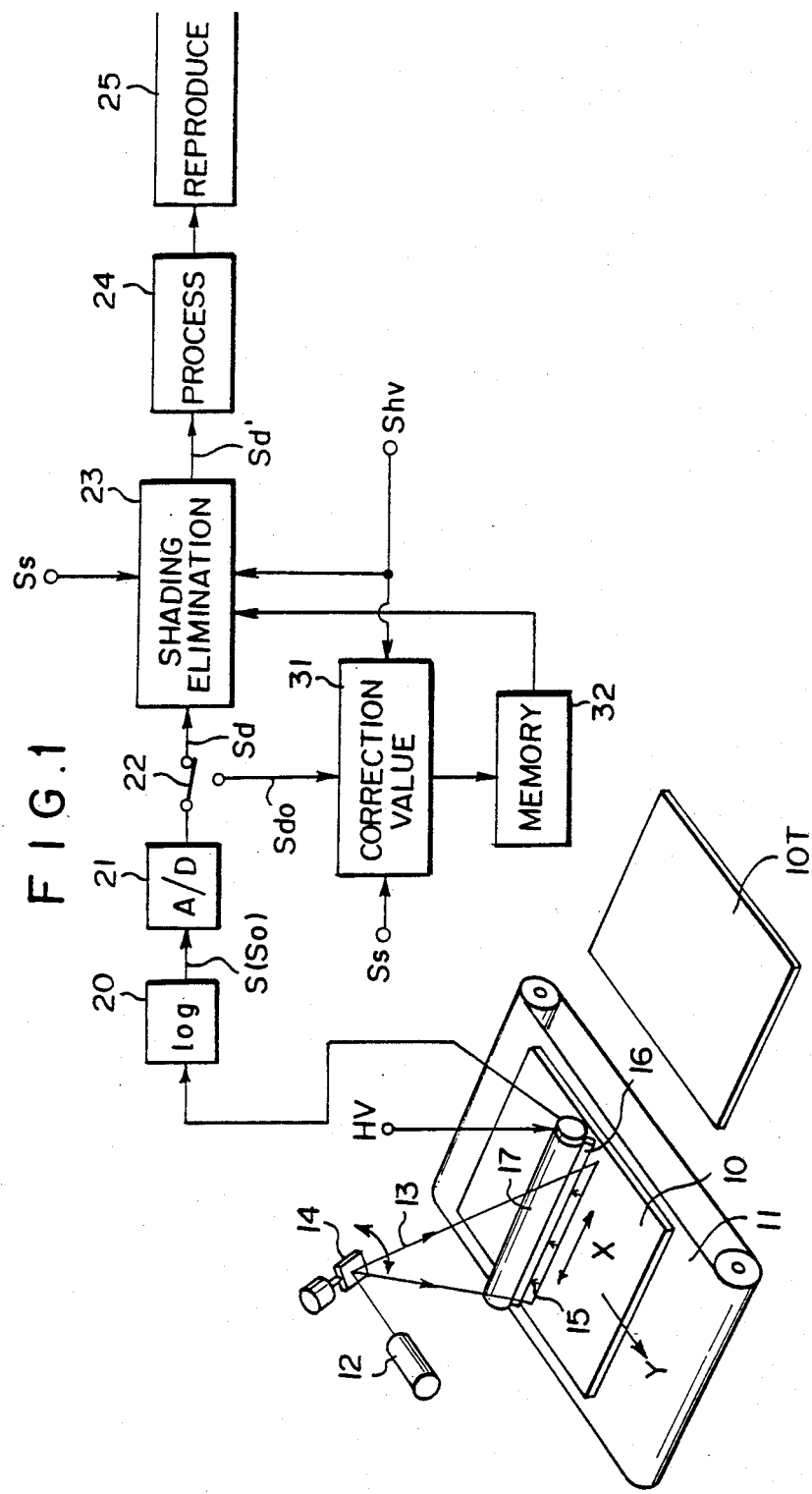
FIG. 1 is a schematic view showing an example of the radiation image read-out apparatus wherein an embodiment of the shading elimination method in accordance with the present invention is employed.

With reference to FIG. 1, an image read-out apparatus shown is constituted as, by way of example, a radiation image read-out apparatus for reading out (detecting) light emitted by a stimulable phosphor sheet in proportion to radiation energy stored thereon in a radiation image recording and reproducing system using the stimulable phosphor sheet as disclosed in, for example, U.S. Pat. No. 4,258,264 and Japanese Unexamined Patent Publication No. 56(1981)-11395. A stimulable phosphor sheet 10 carrying a radiation image stored thereon is conveyed by a sheet conveyance means 11 constituted by an endless belt or the like in the sub-scanning direction as indicated by the arrow Y. Also, a laser beam 13 produced as stimulating rays by a laser beam source 12 is deflected by a light deflector 14 constituted by a galvanometer mirror or the like so as to scan the stimulable phosphor sheet 10 in the main scanning direction as indicated by the arrow X, approximately normal to the sub-scanning direction as indicated by the arrow Y. The portion of the stimulable phosphor sheet 10 exposed to the laser beam 13 emits light 15 in an amount proportional to the stored radiation energy. The emitted light 15 is guided by a light guide member 16 and photoelectrically detected by a photomultiplier 17. In this embodiment, a long photomultiplier provided with a substantially long light detection face extending along a main scanning line of the laser beam 13 on the stimulable phosphor sheet 10 is employed as the photomultiplier 17. The level of the radiation energy stored on the stimulable phosphor sheet 10 may fluctuate largely, for example, as the radiation dose to the stimulable phosphor sheet 10 is changed. In this embodiment, in order to adjust the read-out sensitivity to an appropriate value for the purpose of coping with such fluctuations of the stored radiation energy, the high voltage HV applied to the photomultiplier 17 can be changed over between $-500$ V and $-1,250$ V.

The output of the photomultiplier 17 is subjected to logarithmic conversion and amplification in a logarithmic amplifier 20, and the signals S thus obtained are sent to an A/D converter 21 and converted into digital read-out image signals Sd. The digital read-out image signals Sd thus obtained are sent to an image processing circuit 24 via a switch 22 and a shading elimination circuit 23 which will be described later. The digital read-out image signals Sd are subjected to processing such as gradation processing and frequency response processing in the image processing circuit 24, and are fed to an image reproducing apparatus 25 which may be, for example, a cathode ray tube (CRT) or an optical scanning recording apparatus. The read-out image signals Sd represent the amount of light 15 emitted by the stimulable phosphor sheet 10. Therefore, by use of the read-out image signals Sd, the radiation image was stored on the stimulable phosphor sheet 10 can be reproduced as a visible image by the image reproducing apparatus 25. Instead of immediately feeding the read-out image signals Sd to the image reproducing apparatus 25, the read-out image signals Sd may be temporarily recorded on a recording medium such as a magnetic disk or a magnetic tape.

The long photomultiplier 17 often has non-uniformity of sensitivity in its longitudinal direction. In this case, the output of the photomultiplier 17 fluctuates among different light beam scanning positions in the main scanning direction even though the amount of the light 15 emitted by the stimulable phosphor sheet 10 is the same. Elimination of the fluctuations of the signals S caused by shading will be described hereinbelow.

Figure 2:
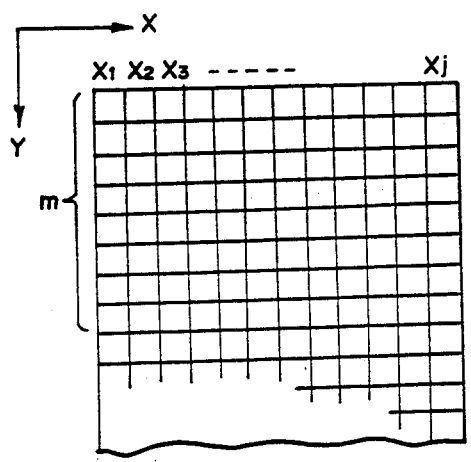
FIG. 2 is an explanatory view showing the shading elimination by the embodiment shown in FIG. 1.

Before the radiation image read-out is carried out as mentioned above, a single stimulable phosphor sheet 10T for test is prepared, and the stimulable phosphor sheet 10T for test is uniformly exposed to a predetermined dose of radiation. The stimulable phosphor sheet 10T for test is then subjected to the same processing as in the case of the aforesaid radiation image read-out in the image read-out apparatus shown in FIG. 1. At this time, the high voltage HV applied to the photomultiplier 17 is adjusted to be $-500$ V. Also, digital reference output signals Sdo obtained by passing the output So of the logarithmic amplifier 20 through the A/D converter 21 are fed to a correction value calculating circuit 31 by change-over of the switch 22. The correction value calculating circuit 31 calculates the fluctuation pattern of the reference output signals Sdo in the main scanning direction of the laser beam 13 as indicated by the arrow X. (The fluctuation pattern is caused by shading, and represents the shading characteristics.) The fluctuation pattern is calculated for each of the picture elements. Specifically, as shown in FIG. 2, in the case where j columns of picture elements are arrayed like $X1, X2, X3, \ldots, Xj$ in the main scanning direction X, a mean value of the reference output signals Sdo at m number of picture elements in the n'column is calculated as a representative signal value Rn of the n'th column. The correction value calculating circuit 31 also receives main scanning position signals Ss generated by a scanning position detection system (not shown) for detecting the main scanning positions of the laser beam 13. Based on the main scanning position signals Ss, the correction value calculating circuit 31 calculates the representative signal values Rn for the respective columns. Then, the correction value calculating circuit 31 calculates differences expressed as $Un=Rn-Ro$ between the respective representative signal values Rn and the mean value Ro of representative signal values $R1, R2, \ldots, Rj$ in the first column to the j'th column. The values $U1, U2, \ldots, Uj$ thus obtained are stored as correction values in a memory 32. The correction value calculating circuit 31 also receives a signal Shv representing the high voltage HV ($-500$ V in this case) of the photomultiplier 17, and stores the correction values U1, U2, ..., Uj to correspond to the high voltage of HV = −500 V in the memory 32.

Thereafter, another stimulable phosphor sheet 10T for test which is of the same type as the aforesaid stimulable phosphor sheet 10T for test is prepared, and the aforesaid operations are repeated by adjusting the high voltage HV to be −1,250 V. At this time, the correction value calculating circuit 31 calculates differences expressed as Wn=Rn−Ro between the representative signal values Rn and the mean value Ro of representative signal values R1, R2, ..., Rj in the first column to the j'th column. The values W1, W2, ..., Wj thus obtained are stored as correction values in the memory 32. In this case, the correction value calculating circuit 31 receives a signal Shv representing the high voltage of HV = −1,250 V of the photomultiplier 17, and stores the correction values W1, W2, ..., Wj to correspond to the high voltage of HV = 1,250 V in the memory 32.

Figure 3:
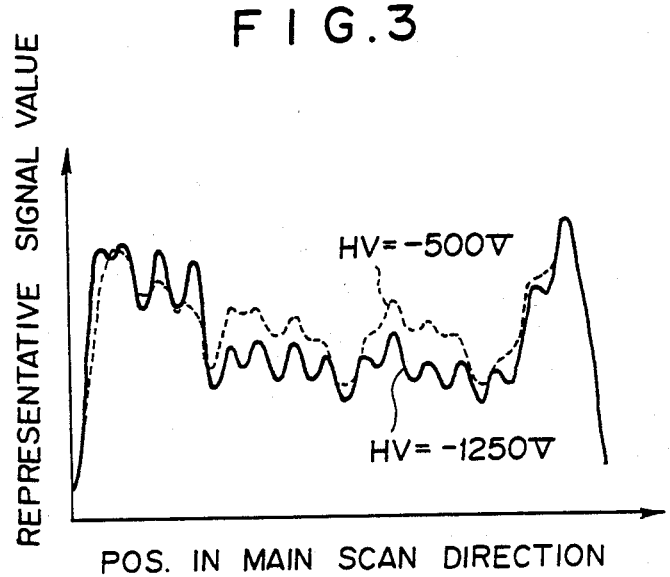
FIG. 3 is a graph showing examples of shading characteristics with respect to levels of high voltage of a photomultiplier.

FIG. 3 shows the conditions of distribution of the representative signal values R1, R2, ..., Rj in the case where HV = −500 V and in the case where HV = −1,250 V. In the case where no shading is present, the representative signal values R1, R2, ..., Rj should be equal to one another. However, actually, shading is present and the representative signal values R1, R2, ..., Rj are not equal to one another. Further, the condition of distribution of the representative signal values R1, R2, ..., Rj at the time HV = −1,250 V is not such that the levels of the representative signal values R1, R2, ..., Rj at the time HV = −500 V are merely changed. Specifically, the sensitivity nonuniformity characteristics of the photomultiplier 17 in its longitudinal direction are different between the case where HV = −500 V and the case where HV = −1,250 V.

In the course of reading out the radiation image stored on the stimulable phosphor sheet 10 in the manner as mentioned above, the digital read-out signals Sd are fed out via the shading elimination circuit 23. The shading elimination circuit 23 reads the correction values U1, U2, ..., Uj or the correction values W1, W2, ..., Wj from the memory 32, and carries out correction wherein the correction values Un or the correction values Wn are subtracted from the digital read-out signals Sd at the picture elements of the n'th column. Said correction is carried out for the read-out signals Sd at all of the picture elements. At this time, the signal Shv representing the high voltage HV of the photomultiplier 17 at the time of the radiation image read-out is fed to the shading elimination circuit 23. The shading elimination circuit 23 reads the correction values U1, U2, ..., Uj from the memory 32 when the high voltage HV which the signal Shv represents is −500 V, reads the correction values W1, W2, ..., Wj from the memory 32 when the high voltage HV which the signal Shv represents is −1,250 V, and use the correction values thus read for the aforesaid correction. In the course of the correction, the main scanning position signals Ss are fed to the shading elimination circuit 23, and the timing of the correction at the respective picture elements is controlled on the basis of the main scanning position signals Ss. As the correction by the subtraction of the correction values Un or the correction values Wn is carried out for the readout signals Sd, changes in the output of the read-out signals Sd caused by shading are compensated for, and the light 15 emitted by the stimulable phosphor sheet 10 can be detected accurately. Therefore, the radiation image which was stored on the stimulable phosphor sheet 10 can be reproduced accurately by use of the corrected read-out signals Sd'.

Also, even though the sensitivity nonuniformity characteristics change in accordance with the high voltage HV of the photomultiplier 17, the aforesaid correction is carried out by use of the correction values Un or the correction values Wn that correspond to the respective shading characteristics. Therefore, in any case, fluctuations in the output of the photomultiplier 17 caused by shading can be compensated for accurately.

In the case where the high voltage HV applied to the photomultiplier 17 is changed continuously or at very small intervals, several sets of correction values (such as the correction values U1, U2, ..., Uj or the correction values W1, W2, ..., Wj) for several levels of the high voltage HV close to the adjusted high voltage may be read from the memory 32, and correction values corresponding to the adjusted high voltage HV may be calculated by interpolating the correction values read from the memory 32 by a known interpolation method. In this case, the number of the correction values stored in the memory 32 can be reduced.

Also, the stimulable phosphor sheet 10T for test need not necessarily be prepared independently for each level of the high voltage HV of the photomultiplier 17. Instead, a single stimulable phosphor sheet 10T for test may be used, the radiation image read-out may be carried out by changing the high voltage HV of the photomultiplier 17 among different portions of the stimulable phosphor sheet 10T for test, and the correction values for shading may be calculated in this manner.

Figure 4:
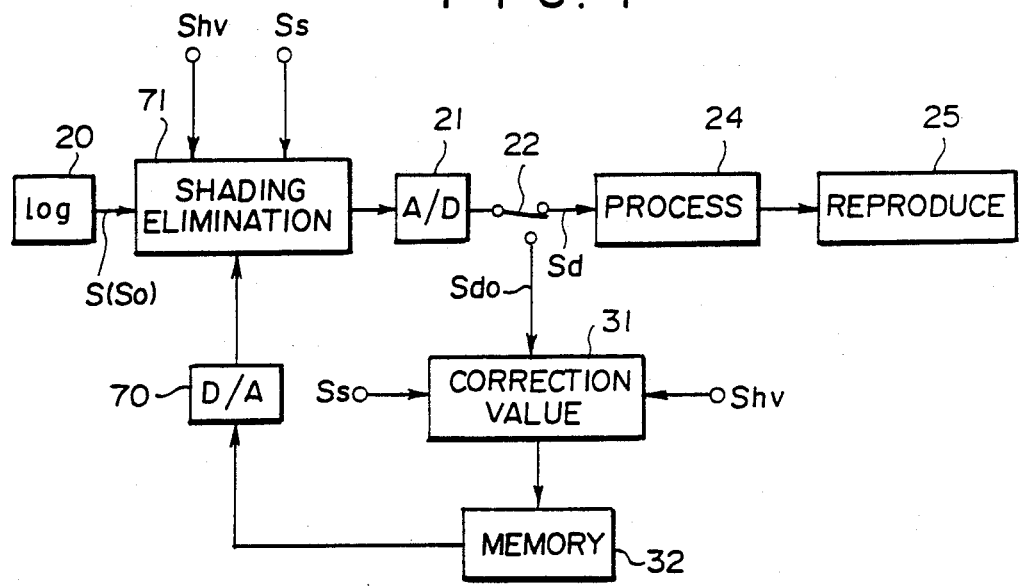
FIG. 4 is a schematic view showing another example of the radiation image read-out apparatus wherein another embodiment of the shading elimination method in accordance with the present invention is employed.

In the aforesaid embodiment, the elimination of shading is carried out for the digitized read-out signals Sd. However, as shown in FIG. 4, the correction values U1, U2, ..., Uj or the correction values W1, W2, ..., Wj read from the memory 32 may be converted by a D/A converter 70 into analog correction signals, and the analog correction signals may be subtracted from the analog read-out signals S by a shading elimination circuit 71 provided at the stage prior to the A/D converter 21. In this case, the resolution of the correction can be increased. In FIG. 4, similar elements are numbered with the same reference numerals with respect to FIG. 1.

Figure 5:
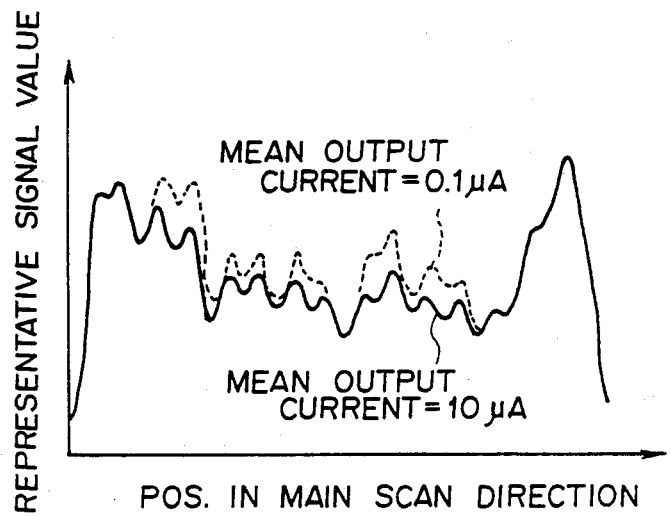
FIG. 5 is a graph showing examples of shading characteristics with respect to levels of mean output current of a photomultiplier.

A further embodiment of the shading elimination method in accordance with the present invention will be described hereinbelow. FIG. 5 shows examples of the conditions of distribution of the representative signal values R1, R2, ..., Rj in the case where the high voltage HV is fixed at −1,000 V and mean output current is adjusted to be 0.1 μA and 10 μA by changing the intensity of light incident upon the photomultiplier. Also, in this case, shading arises and the shading characteristics change as the intensity of the incident light is changed, i.e. as the level of the optical amount of the light 15 emitted by the stimulable phosphor sheet 10 varies.

FIG. 6 shows an embodiment wherein the elimination of shading is carried out by considering fluctuations of the shading characteristics in accordance with the optical amount of the light 15 emitted by the stimulable phosphor sheet 10. In FIG. 6, similar elements are numbered with the same reference numerals with respect to FIG. 1. In this case, instead of the stimulable phosphor sheet 10T for test uniformly exposed to radiation, a stimulable phosphor sheet 10T' for test on which the radiation dose is changed among a plurality of portions 10a, 10b, 10c, 10d, 10e and 10f arrayed in the direction of subscanning sheet feed is used. In this embodiment, the portion 10a of the stimulable phosphor sheet 10T' for test is exposed to the largest radiation dose, and the radiation dose is decreased step-wise in the sequence of the portion 10b, 10c, and so on. The portion 10f is exposed to no radiation dose. As in the aforesaid embodiments, the stimulable phosphor sheet 10T' for test is subjected to read-out processing prior to ordinary radiation image read-out processing. At this time, the high voltage HV applied to the photomultiplier 17 is first adjusted to be −500 V. The digital reference output signals Sdo obtained by readout processing are fed to a correction value calculating circuit 80 via the switch 22. The correction value calculating circuit 80 calculates the correction values U1, U2, ..., Uj on the basis of the received reference output signals Sdo. A total of six sets of the correction values U1, U2, ..., Uj are obtained for the portions 10a to 10f of the stimulable phosphor sheet 10T' for test on which readout processing is carried out.

Thereafter, another stimulable phosphor sheet 10T' for test which is of the same type as the aforesaid stimulable phosphor sheet 10T' for test is prepared, and read-out processing is carried out on the stimulable phosphor sheet 10T' for test by changing the high voltage HV to −1,250 V. Also, in this case, a total of six sets of the correction values W1, W2, ..., Wj are obtained for the portions 10a to 10f of the stimulable phosphor sheet 10T' for test.

In this embodiment, a table of the correction values is obtained by using the high voltage HV and the radiation dose to the stimulable phosphor sheet 10T'for test, i.e. the level of the optical amount of the light 15 emitted by the stimulable phosphor sheet 10T' for test, as two-dimensional parameters. The correction values are stored in a memory 81 to correspond to high voltage HV and the output signals Sdo which represent the levels of the optical amount of the light 15 emitted by the stimulable phosphor sheet 10T' for test.

Thereafter, in the course of reading out the radiation image stored on the stimulable phosphor sheet 10, the digital read-out signals Sd are fed out via the shading elimination circuit 82. The shading elimination circuit 82 reads the correction values U1, U2, ..., Uj or the correction values W1, W2, ..., Wj from the memory 81, and carries out correction wherein the correction values Un or the correction values Wn are subtracted from the digital read-out signals Sd at the picture elements of the n'th column. Said correction is carried out for the read-out signals Sd at all of the picture elements. At this time, the signal Shv representing the high voltage HV of the photomultiplier 17 at the time of the radiation image readout is fed to the shading elimination circuit 82. The shading elimination circuit 82 reads the correction values U1, U2, ..., Uj from the memory 81 when the high voltage HV which the signal Shv represents is −500 V, and reads the correction values W1, W2, ..., Wj from the memory 81 when the high voltage HV which the signal Shv represents is −1,250 V. As mentioned above, six sets of the correction values U1, U2, ..., Uj and six sets of the correction values W1, W2, ..., Wj are stored in the memory 81. In accordance with the values of the received read-out signals Sd, the shading elimination circuit 82 reads the correction values which are stored to correspond to the signals Sdo of the same values as the read-out signals Sd. The read-out signals Sd attain more than six different values, for example, 256 levels (=8 bits) of values. Therefore, the read-out signals Sd may attain intermediate values among the six levels of the signals Sdo corresponding to the correction values U1, U2, ..., Uj and the correction values W1, W2, ..., Wj. In such a case, the shading elimination circuit 82 carries out known interpolation processing by use of two levels of the signals Sdo exactly larger than and smaller than the respective read-out signals Sd, and calculates the correction values U1, U2, ..., Uj or the correction values W1, W2, ..., Wj that correspond to the read-out signals Sd. Alternatively, the correction values U1, U2, ..., Uj or the correction values W1, W2, ..., Wj obtained after interpolation processing carried out in the manner as mentioned above may be stored in advance in the memory 81. In this case, interpolation processing need not be carried out at the time of shading elimination, though a large-capacity memory is required as the memory 81.

Correction is then carried out by subtracting the correction values Un or the correction values Wn, which are read or calculated in the manner as mentioned above, from the digital read-out signals Sd. In this manner, in this embodiment, fluctuations in the output of the photomultiplier 17 caused by shading can be compensated for accurately even though the high voltage HV and the level of the optical amount of the light emitted by the stimulable phosphor sheet 10 fluctuate in various manners.

The shading elimination method in accordance with the present invention is applicable not only to the apparatus for detecting the light 15 emitted by the stimulable phosphor sheet 10, but also to any other image read-out apparatuses for detecting light reflected by a recording medium or light passing through the recording medium, which light carries the image recorded on the recording medium.

I claim:

1. A shading elimination method in an image readout apparatus for scanning a light beam on a recording medium carrying an image recorded thereon, obtaining light which carries the image by the scanning, and detecting the light by use of a photomultiplier to obtain read-out signals carrying the image, the shading elimination method in an image readout apparatus which comprises the steps of:

(i) detecting the shading characteristics in the direction of main scanning of said light beam by changing the level of high voltage applied to said photomultiplier to a plurality of levels prior to said detection of said light, (ii) storing said shading characteristics to correspond to said levels of said high voltage in a storage means, (iii) detecting the level of said high voltage at the time of said detection of said light, and reading said shading characteristics that correspond to the detected level of said high voltage from said storage means, and (iv) correcting said read-out signals in accordance with said shading characteristics read from said storage means so that changes in the output of said photomultiplier caused by the shading are eliminated.

2. A method as defined in claim 1 wherein the shading characteristics in the direction of main scanning of said light beam are detected by changing the level of high voltage applied to said photomultiplier to a plurality of levels and by changing the level of the optical amount of the light obtained by the scanning of the recording medium to a plurality of levels prior to said detection of said light, said shading characteristics are stored in said storage means to correspond to said levels of said high voltage and said levels of the optical amount of the light obtained by the scanning of the recording medium, the level of said high voltage and the level of the optical amount of the light obtained by the scanning are detected at the time of said detection of said light, and said shading characteristics that correspond to the detected level of said high voltage and to the detected level of the optical amount of the light obtained by the scanning are read from said storage means.

3. A method as defined in claim 1 or 2 wherein said recording medium is a stimulable phosphor sheet carrying a radiation image stored thereon as said image, and said light obtained by the scanning is light emitted by said stimulable phosphor sheet in proportion to the stored radiation energy when said stimulable phosphor sheet is scanned by stimulating rays as said light beam.

4. A method as defined in claim 1 or 2 wherein said photomultiplier is a long photomultiplier.

* * * * *